United States Patent
Ahlquist et al.

(10) Patent No.: US 8,722,330 B2
(45) Date of Patent: May 13, 2014

(54) COLLECTING AND PROCESSING COMPLEX MACROMOLECULAR MIXTURES

(75) Inventors: David A. Ahlquist, Rochester, MN (US); Jonathan J. Harrington, Madison, WI (US); Hongzhi Zou, Middleton, WI (US); Patrick S. Quint, Kasson, MN (US); William R. Taylor, Lake City, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 5 days.

(21) Appl. No.: 13/531,017

(22) Filed: Jun. 22, 2012

(65) Prior Publication Data
US 2012/0288956 A1  Nov. 15, 2012

Related U.S. Application Data

(63) Continuation of application No. 12/555,672, filed on Sep. 8, 2009, now abandoned.

(60) Provisional application No. 61/094,770, filed on Sep. 5, 2008.

(51) Int. Cl.
*C12Q 1/68* (2006.01)
*C12N 5/00* (2006.01)
*C12N 5/02* (2006.01)

(52) U.S. Cl.
USPC ............................ 435/6.1; 435/325; 435/374

(58) Field of Classification Search
CPC .......... C12Q 1/6806; C12Q 1/28; C12Q 1/68; C12Q 1/6832; C12Q 2326/12; G01N 1/38; G01N 1/40; G01N 33/581
USPC ....................................... 435/6, 6.1, 325, 374
See application file for complete search history.

(56) References Cited

U.S. PATENT DOCUMENTS

| | | | |
|---|---|---|---|
| 4,741,437 A | | 5/1988 | Gorski et al. |
| 4,789,630 A | * | 12/1988 | Bloch et al. ..................... 435/5 |
| 5,149,506 A | | 9/1992 | Skiba et al. |
| 6,084,091 A | * | 7/2000 | Muller et al. ................. 536/25.4 |
| 6,090,935 A | | 7/2000 | Breivik et al. |
| 6,133,436 A | | 10/2000 | Koster |
| 2002/0037512 A1 | * | 3/2002 | Baker ................................ 435/6 |
| 2005/0042675 A1 | * | 2/2005 | Lakner et al. .................. 435/7.1 |
| 2006/0264510 A1 | * | 11/2006 | Halstead et al. ............... 514/566 |
| 2008/0025877 A1 | | 1/2008 | Alley |

OTHER PUBLICATIONS

Zwittergent Reagents from Santa Cruz Biotechnology, Inc. [retrieved on Aug. 22, 2013]. Retrieved from the Internet: <URL: www.scbt.com/display.php?search_catalog=zwittergent).*
Calbiochem Catalog Item # 693023 provided by emdmillpore.com, retrieved on Nov. 14, 2013.*
Jarnum and Peterson, "Protein-losing enteropathy", 1961, Lancet, 25(1):417-21.

(Continued)

*Primary Examiner* — Robert T. Crow
(74) *Attorney, Agent, or Firm* — Casimir Jones SC

(57) ABSTRACT

This document provides methods and materials involved in collecting and processing complex macromolecular mixtures (e.g., stool samples). For example, stool collection devices, buffers for stabilizing nucleic acid and polypeptides present in stool, and kits for using sequence-specific capture probes (e.g., nucleic acid sequences designed to hybridize with particular target nucleic acids) to capture target nucleic acids directly from complex macromolecular mixtures (e.g., stool samples) without the need to perform prior steps to enrich, isolate, or purify the nucleic acid component are provided.

9 Claims, 6 Drawing Sheets

(56) References Cited

OTHER PUBLICATIONS

Kurasawa et al., "Plant residue and bacteria as bases for increased stool weight accompanying consumption of higher dietary fiber diets", 2000, J. Am. Coll. Nutr., 19(4):426-433.

Peranio and Bruger, "The detection of occult blood in feces including observations on the ingestion of iron and whole blood", 1951, J. Lab. Clin. Med., 38(3):433-45.

Walsh and Terdiman, "Colorectal cancer screening: scientific review", 2003, JAMA, 289:1288-1296.

Zou et al., "A sensitive method to quantify human long DNA in stool: relevance to colorectal cancer screening", 2006, Cancer Epidemiol Biomarkers Prev, 15(6):1115-9.

International Search Report and Written Opinion dated Mar. 3, 2010, International Patent Application No. PCT/US2009/056252.

* cited by examiner

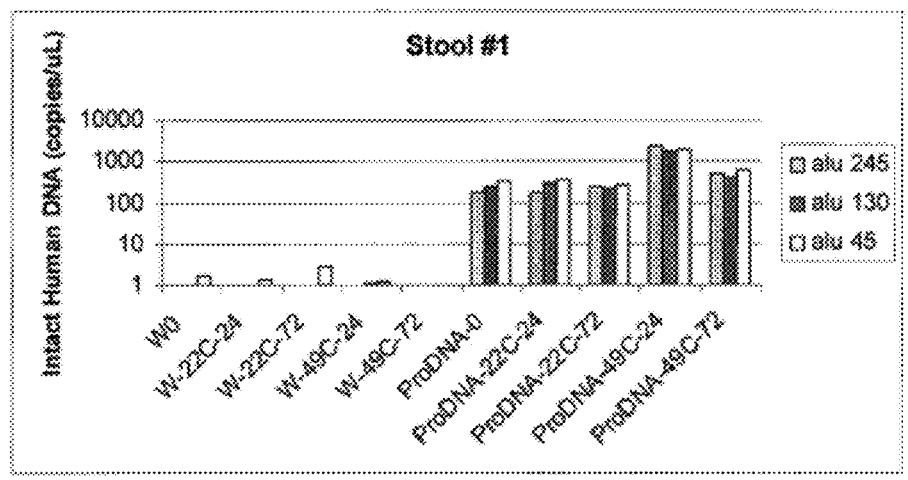
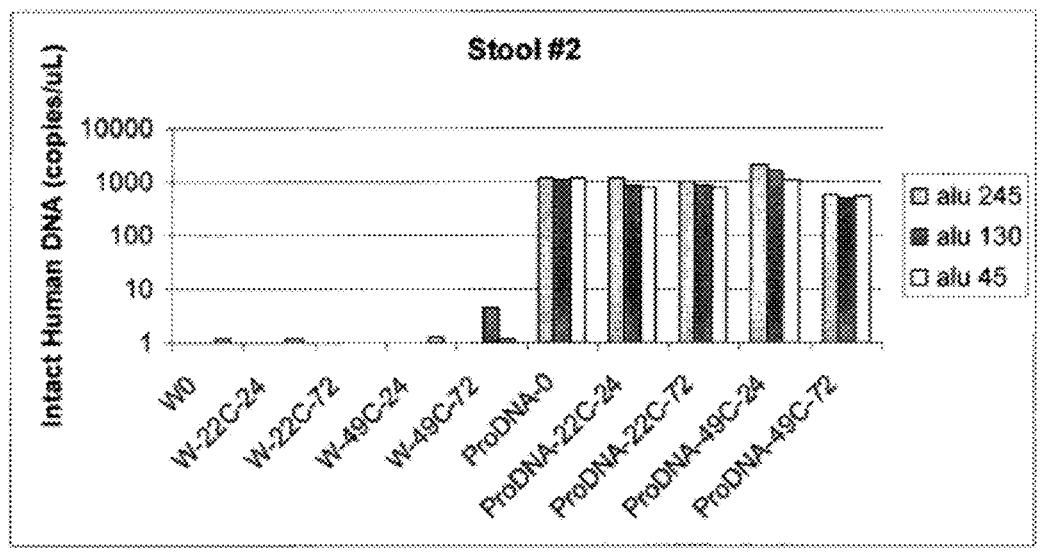

SEQUENCE LISTING

<160> NUMBER OF SEQ ID NOS: 9

<210> SEQ ID NO 1
<211> LENGTH: 37
<212> TYPE: DNA
<213> ORGANISM: Artificial Sequence
<220> FEATURE:
<223> OTHER INFORMATION: Synthetic

<400> SEQUENCE: 1
cagatagccc tggacaaacc atgccaccaa gcagaag     37

<210> SEQ ID NO 2
<211> LENGTH: 37
<212> TYPE: DNA
<213> ORGANISM: Artificial Sequence
<220> FEATURE:
<223> OTHER INFORMATION: Synthetic

<400> SEQUENCE: 2
ttccagcagt gtcacagcac cctagaacca aatccag     37

<210> SEQ ID NO 3
<211> LENGTH: 39
<212> TYPE: DNA
<213> ORGANISM: Artificial Sequence
<220> FEATURE:
<223> OTHER INFORMATION: Synthetic

<400> SEQUENCE: 3
atgacaatgg gaatgaaaca gaatcagagc agcctaaag     39

<210> SEQ ID NO 4

```
<211> LENGTH: 21
<212> TYPE: DNA
<213> ORGANISM: Artificial Sequence
<220> FEATURE:
<223> OTHER INFORMATION: Synthetic

<400> SEQUENCE: 4
ttcattatct ttgtcatcag c                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cgctcctgaa gaaaattcaa                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
caggagaccc cactcatgtt                                                20

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
tggcaaaatg taataaagta tcagc                                          25

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
gagcctcgat gagccattta                                                20

<210> SEQ ID NO 9
<211> LENGTH: 26
<212> TYPE: DNA
<213> ORGANISM: Artificial Sequence
<220> FEATURE:
<223> OTHER INFORMATION: Synthetic

<400> SEQUENCE: 9
tcaatatcat catcatctga atcatc                                         26
```

COLLECTING AND PROCESSING COMPLEX MACROMOLECULAR MIXTURES

CROSS-REFERENCE TO RELATED APPLICATIONS

This application is a continuation of pending U.S. patent application Ser. No. 12/555,672, filed Sep. 8, 2009, which claims the benefit of expired Provisional Patent Application No. 61/094,770, filed Sep. 5, 2008, the contents of which are incorporated by reference in their entireties.

BACKGROUND

1. Technical Field

This document relates to methods and materials involved in collecting and processing complex macromolecular mixtures (e.g., stool samples).

2. Background Information

Human stool is composed primarily of materials that are not digested or are not absorbed. Human stools are roughly 75 percent water and 25 percent solid matter (Kurasawa et al., *J. Am. Coll. Nutr.*, 19(4):426-433 (2000)). The solid matter, which makes up the fecal dry weight, includes roughly 30-50 percent bacteria, 30-40 percent undigestible food constituents such as cellulose and extra fibers, and variable amounts of organic wastes including fats.

The soluble, aqueous phase of stool is a diagnostically relevant constituent of stool from which can be derived pathologically important biomarkers. Several biochemical assays exist for the determination of colon disease, including measurement of fecal occult blood for the detection of colorectal cancer (Walsh and Terdiman, *JAMA*, 289:1288-1296 (2003) and Peranio and Bruger, *J. Lab. Clin. Med.*, 38(3):433-45 (1951)), an assay for the detection of protein loosing enteropathy (Jarnum and Peterson, Lancet, 25(1):417-21 (1961)), and assays designed to capture fecal DNA and determine its use in pathological diagnosis.

SUMMARY

This document relates to methods and materials involved in collecting and processing complex macromolecular mixtures (e.g., stool samples). For example, this document provides stool collection devices, buffers for stabilizing nucleic acid and polypeptides present in stool, and kits for using sequence-specific capture probes (e.g., nucleic acid sequences designed to hybridize with particular target nucleic acids) to capture target nucleic acids directly from complex macromolecular mixtures (e.g., stool samples) without the need to perform prior steps to enrich, isolate, or purify the nucleic acid component.

In general, one aspect of this document features a device for a stool sample. The device comprises, or consists essentially of, a container for housing a buffer and collected stool sample, and a lid for closing the buffer and collected stool sample within the container, wherein the lid comprises a stool handling extension and a sealable port. The container can comprise a piercable membrane configured to retain the buffer within the container. The container can be a tube. The lid can be configured to engage the container via threads. The stool handling extension is not limited to a particular shape and/or design. In some embodiments, the stool handling extension comprises a spatula for scooping stool. In some embodiments, the stool handling extension is configured to collect, retain and deliver a stool sample (e.g., deliver to a container of the present invention). In some embodiments, the stool handling extension has a ladle design (i.e., having a handle terminating in a bowl shape, with the bowl shape oriented at an angle (e.g., 10 degrees, 20 degrees, 30 degrees, 40 degrees, 50 degrees, 60 degrees, 70 degrees, 80 degrees, etc.) to the handle). In some embodiments, the stool handling extension has a spoon design. In some embodiments, the stool handling extension has a bevel design. In some embodiments, the stool handling extension has teeth (e.g., 1, 2, 3, 5, 10, 50, 100 teeth) so as to ease collection, retention and delivery of a stool sample. In some embodiments, the stool handling extension can be removably attached to the lid.

In another aspect, this document features a method for collecting a stool sample with a device comprising a container for housing a buffer and collected stool sample, and a lid for closing the buffer and collected stool sample within the container, wherein the lid comprises a stool handling extension and a sealable port, wherein the method comprises, or consisting essentially of: (a) handling the lid to collect the stool sample from stool via the stool handling extension, and (b) attaching the lid onto the container, thereby placing the stool sample within the container.

In another aspect, this document features a buffer comprising, or consisting essentially of, between about 100 to about 300 mM of CDTA (e.g., 50 mM CDTA, 100 mM CDTA, 125 mM CDTA, 150 mM CDTA, 190 mM CDTA, 225 mM CDTA, 275 mM CDTA, 300 mM CDTA, 310 mM CDTA, 350 mM CDTA), between about 400 and about 600 mM of tris hydrochloride (e.g., 350 mM of tris hydrochloride, 390 mM of tris hydrochloride, 400 mM of tris hydrochloride, 425 mM of tris hydrochloride, 475 mM of tris hydrochloride, 510 mM of tris hydrochloride, 550 mM of tris hydrochloride, 590 mM of tris hydrochloride, 600 mM of tris hydrochloride, 620 mM of tris hydrochloride, 650 mM of tris hydrochloride), between about 5 and about 15 mM of NaCl (e.g., 3.5 mM of NaCl, 5 mM of NaCl, 6 mM of NaCl, 9 mM of NaCl, 12 mM of NaCl, 15 mM of NaCl, 16 mM of NaCl, 18 mM of NaCl), and between about 0 and about 0.075% of a zwitterionic reagent (e.g., 0% of a zwitterionic reagent, 0.025% of a zwitterionic reagent, 0.05% of a zwitterionic reagent, 0.075% of a zwitterionic reagent, 0.08% of a zwitterionic reagent).

In another aspect, this document features a method for stabilizing nucleic acid and polypeptides within a stool sample, wherein the method comprises, or consisting essentially of, contacting the stool sample with a buffer comprising between about 100 to about 300 mM of CDTA, between about 400 and about 600 mM of tris hydrochloride, between about 5 and about 15 mM of NaCl, and between about 0 and about 0.075% of a zwitterionic reagent.

In another aspect, this document features a method for obtaining target nucleic acid from a complex macromolecular mixture without performing a prior nucleic acid extraction or nucleic acid isolation step, wherein the method comprises, or consists essentially of: (a) contacting the complex macromolecular mixture with a sequence-specific capture probe comprising one member of a binding pair to form a probe/target nucleic acid complex if the complex macromolecular mixture comprises the target nucleic acid, (b) contacting the probe/target nucleic acid complex with magnetic material comprising another member of the binding pair to form a magnetic probe/target nucleic acid complex if the probe/target nucleic acid complex is formed in (a), and (c) applying magnetic force to isolate the magnetic probe/target nucleic acid complex from the complex macromolecular mixture if the magnetic probe/target nucleic acid complex is formed in (b). The complex macromolecular mixture can be a stool sample. The method can be performed without a prior phenol/chloroform extraction. In some embodiments, the one member of the binding pair can comprise biotin. In some embodiments, the other member of the binding pair can be streptavidin. The magnetic material can be a bead. The method can comprise isolating the target nucleic acid from the isolated magnetic probe/target nucleic acid complex of step (d).

In some embodiments, the sequence-specific capture probes include additional components to aid in isolation. For example, in some embodiments, a sequence-specific capture probe provided herein can include biotin, sequence tags, fluorescent labels, cleavage sites or any other directly or indirectly detectable moiety or feature. In some cases, a sequence-specific capture probe provided herein can include a spacer sequence. For example, a sequence-specific capture probe provided herein can contain biotin followed by a molecular spacer (e.g., 5, 6, 7, 8, 9, 10, 11, 12, 13, 14, 15, 16, 17, 18, 19, or 20 carbon atoms) followed by a nucleic acid sequences designed to hybridize with particular target nucleic acids. In some cases, a sequence-specific capture probe provided herein can contain a nucleic acid sequences designed to hybridize with particular target nucleic acids followed by a molecular spacer followed by biotin. The sequence-specific probe is not limited to a particular length. For example, in some embodiments, the probe length is between 35-55 nucleic acid bases (e.g., 30 bases, 35 bases, 40 bases, 42 bases, 50 bases, 54 bases, 55 bases, 60 bases).

The devices, buffers, and methods are configured to use any and all types and/or kinds of stool samples. Indeed, the device is configured for collecting, retention and delivery of any type of stool, such as, for example, separate hard lumped stool (e.g., like nuts), sausage-shaped stool, sausage-like stool with cracks on its surface, stool shaped like a snake, soft blobbed stool with clear cut edges, fluffy pieced stool with ragged edges, and watery/liquid stool (e.g., diarrhea).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 6 contains histograms demonstrating the effects of time and temperature on the stability of DNA in stool. Stool samples from two normal individuals were incubated in either water or ProDNA buffer at a 1:7 dilution at 24° C. and 49° C. Aliquots were taken at 0 and 3 days, extracted, and subjected to real-time PCR using human alu specific primers at 3 different amplicon lengths –45, 130, and 245 bp. Results were normalized to human DNA standards.

DETAILED DESCRIPTION

This document provides methods and materials that can be used to collect stool sample for analysis. For example, this document provides a stool collection device. Stool samples collected using such a stool collection device provided herein can be used for colorectal cancer screening, screening for any aerodigestive cancer or precancer, diagnosing gastrointestinal infectious disease (e.g., bacterial enterocolitides, viral gastroenteritis, *H. pylori* gastritis, giardiasis, hook worm, or other parasitic infestations), diagnosing non-infectious, non-neoplastic gastrointestinal diseases (e.g., Sprue, fat malabsorption, lactose intolerance, other carbohydrate malabsorption, protein-losing enteropathy, eosinophic gastroenteritis, pancreatic insufficiency, GI bleeding, or ischemic bowel disease), or forensic applications (e.g., determining recent dietary intake).

Figure 1:
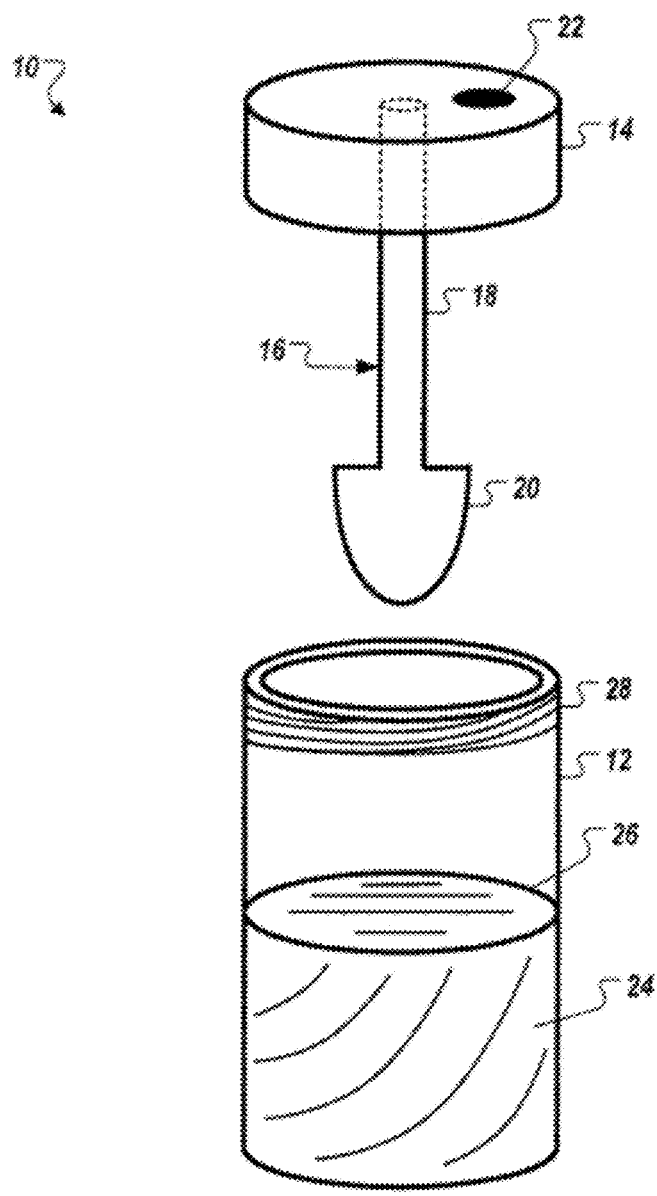
FIG. 1 is a side view of one example of a stool collection device.

In reference to FIG. 1, device 10 can contain container 12 and lid 14. Container 12 can be any shape provided that it can house a buffer and collected stool sample. In some cases, container 12 can be a tube (e.g., a 50 mL tube). Container 12 can include threads 28, which can mate with threads within lid 14 (not shown). Such mating can seal the contents within device 10 without leaking. Container 12 can include a liquid buffer 24 (e.g., a sample stabilization or extraction buffer). Container 12 can include a piercable membrane 26. Piercable membrane 26 can be designed to retain buffer 24 within the lower region of container 12.

Figure 2:
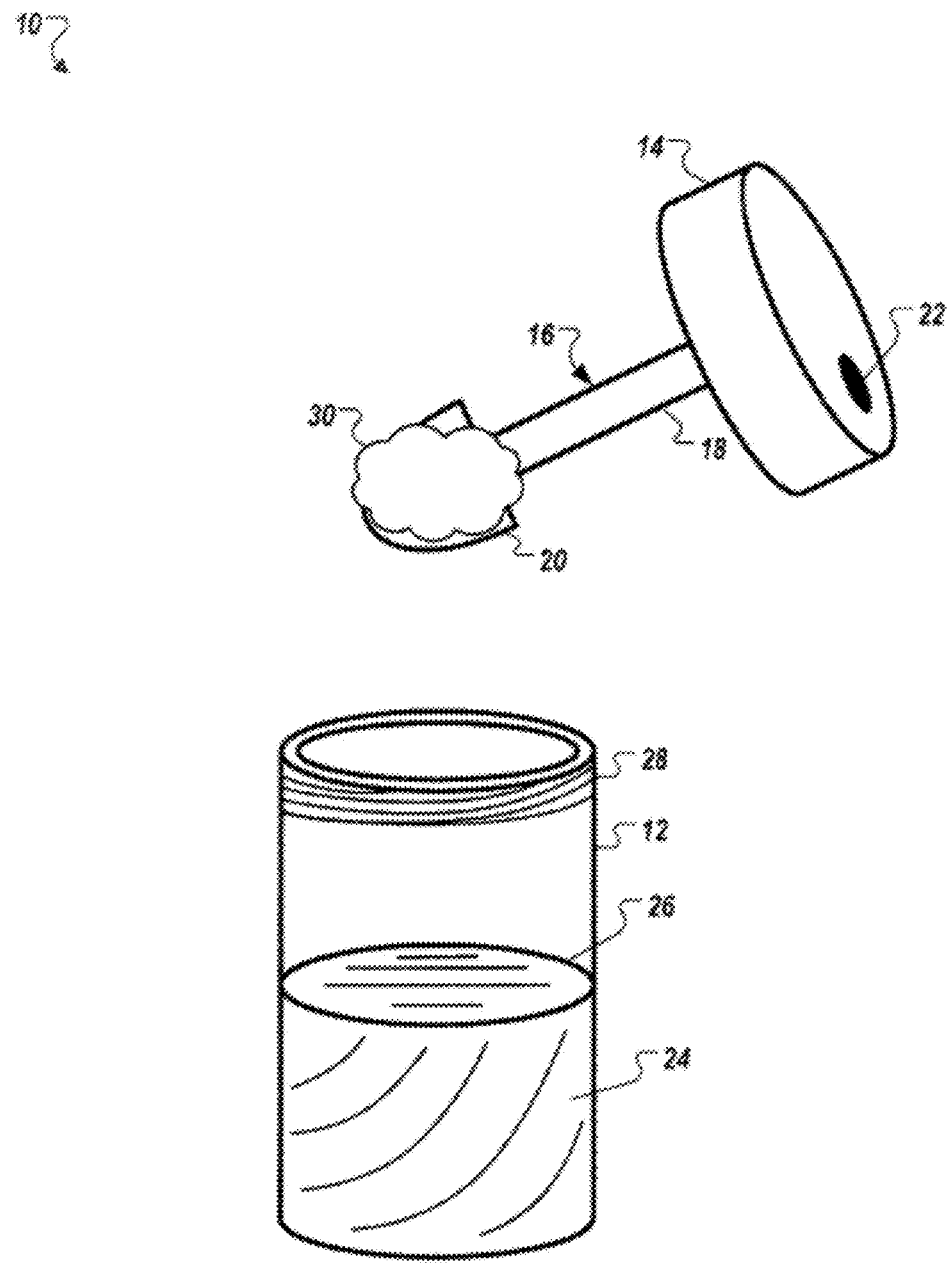
FIG. 2 is a side view of the stool collection device of FIG. 1 during the stool collection process.
Figure 3:
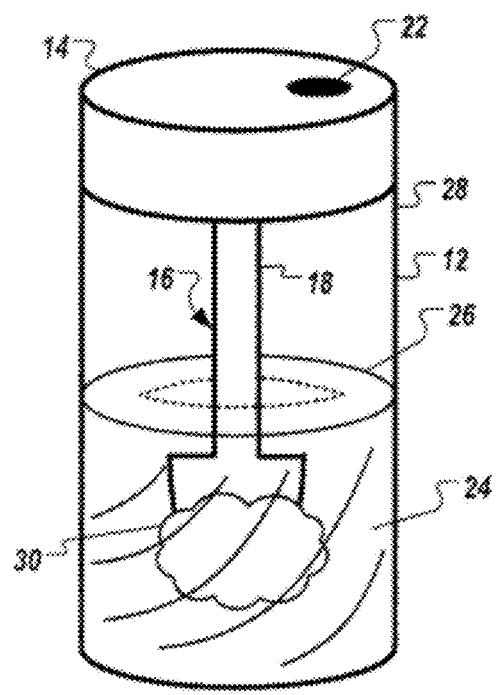
FIG. 3 is a side view of the stool collection device of FIG. 1 after a stool sample is placed inside the device.

With further reference to FIG. 1, lid 14 can be a screw-top for container 12. In some cases, lid 14 can include a stool handling extension 16. Stool handling extension 16 can include a shaft 18 and a spatula region 20. Spatula region 20 can be designed to scoop a portion of a stool sample that is to be placed within device 10. In some cases, a stool handling extension can include a stool coring region. In some cases, stool handling extension 16 can be designed such that full engagement of lid 14 onto container 12 results in stool handling extension 16 piercing piercable membrane 26. Thus, in use, the act of placing lid 14 with spatula region 20 containing a stool sample onto container 12 can result in piercing piercable membrane 26 and allowing the stool sample to mix with buffer 24 (FIGS. 2 and 3). In some cases, lid 14 can contain port 22. Port 22 can provide access to a buffer/stool mixture housed within container 12 in a manner that avoids leaking. In some cases, port 22 can be covered with a removable cap. For example, port 22 can be a sealable entry point for a needle or needle-less syringe. In some cases, container 12 can lack piercable membrane 26, and buffer 24 can be added to container 12 via port 22 after lid 14 seals device 10 closed.

Figure 4:
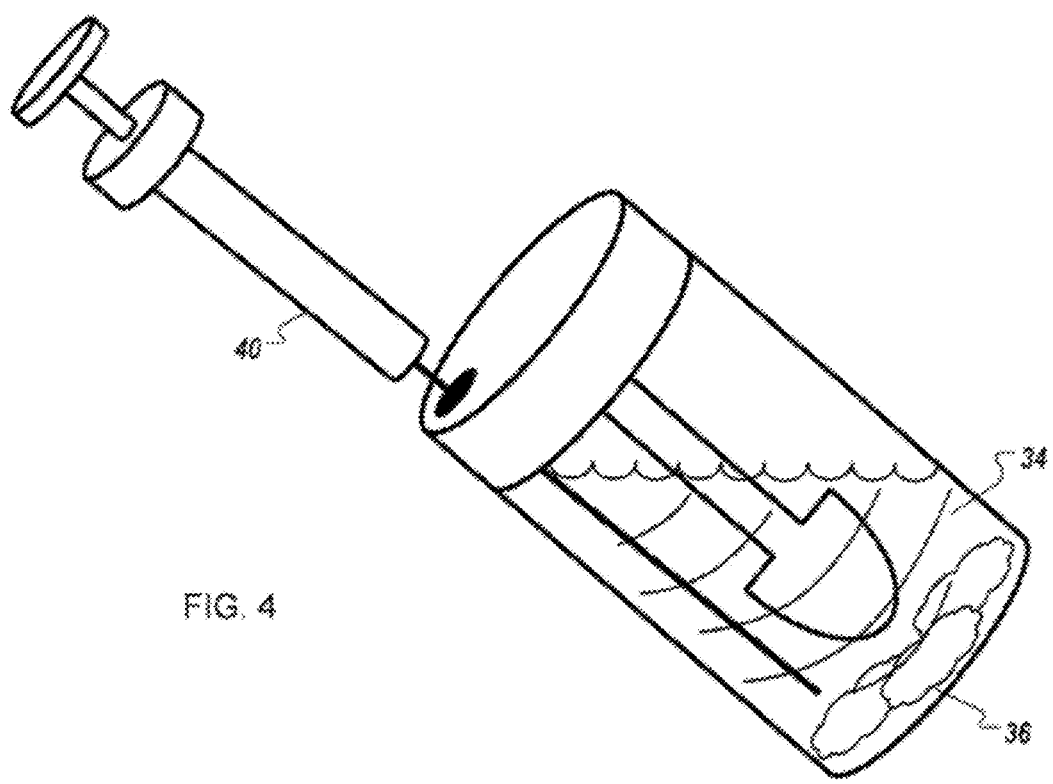
FIG. 4 is a side view of the stool collection device of FIG. 1 during the sample retrieval process.

Once a stool sample is placed into device 10 and lid 14 seals container 12, device 10 can be shipped to a clinic for analysis. As shown in FIG. 4, the device 10 can be centrifuged so that particulate material 36 collects on the bottom of container 12. The supernatant 34 can be retrieved from the container via port 22 using, for example, a needle or needle-less syringe 40. In some cases, the contents of device 10 can be filtered as opposed to be centrifuged.

The stool handling extension is not limited to a particular shape and/or design. In some embodiments, the stool handling extension comprises a spatula for scooping stool. In some embodiments, the stool handling extension is configured to collect, retain and deliver a stool sample (e.g., deliver to a container of the present invention). In some embodiments, the stool handling extension has a ladle design. In some embodiments, the stool handling extension has a spoon design. In some embodiments, the stool handling extension has a bevel design. In some embodiments, the stool handling extension has teeth (e.g., 1, 2, 3, 5, 10, 50, 100 teeth) so as to ease collection, retention and delivery of a stool sample. In some embodiments, the stool handling extension can be removably attached to the lid.

This document also provides buffers for stabilizing nucleic acid and polypeptides present in stool. Such buffers can contain between about 100 and about 300 mM of a chelating reagent (e.g., EDTA, CDTA) (e.g., 50 mM CDTA, 100 mM CDTA, 125 mM CDTA, 150 mM CDTA, 190 mM CDTA, 225 mM CDTA, 275 mM CDTA, 300 mM CDTA, 310 mM CDTA, 350 mM CDTA), between about 400 and about 650 mM of tris hydrochloride (e.g., 350 mM of tris hydrochloride, 390 mM of tris hydrochloride, 400 mM of tris hydrochloride, 425 mM of tris hydrochloride, 475 mM of tris hydrochloride, 510 mM of tris hydrochloride, 550 mM of tris hydrochloride, 590 mM of tris hydrochloride, 600 mM of tris hydrochloride, 620 mM of tris hydrochloride, 650 mM of tris hydrochloride), between about 5 and about 15 mM of NaCl (e.g., 3.5 mM of NaCl, 5 mM of NaCl, 6 mM of NaCl, 9 mM of NaCl, 12 mM of NaCl, 15 mM of NaCl, 16 mM of NaCl, 18 mM of NaCl), and between about 0 and about 0.075% of a zwitterionic reagent (e.g., 0% of a zwitterionic reagent, 0.025% of a zwitterionic reagent, 0.05% of a zwitterionic reagent, 0.075% of a zwitterionic reagent, 0.08% of a zwitterionic reagent). For example, a buffer provided herein can contain 0.5 M Tris hydrochloride, 150 mM CDTA, 10 mM NaCl, and 0.05% Zwittergent 6-13.

This document also provides methods and materials that can be used for the direct capture of specific nucleic acids (e.g., DNA or RNA molecules) from complex macromolecular mixtures (e.g., stool, blood, urine, bile, saliva, or tissue homogenates).

In general, the methods provided herein can include using sequence-specific capture probes (e.g., nucleic acid sequences designed to hybridize with particular target nucleic acids) to anneal with particular target sequences present in a complex macromolecular mixture. In some cases, sequence-specific capture probes can include additional components to aid in isolation. For example, a sequence-specific capture probe provided herein can include biotin, sequence tags (e.g., sequence tags specific for types of cancer) (e.g., kras codon 12 mutations, vimentin CpG hypermethylation, Bat26 MSI, and APC exon 15 insertion/deletions), fluorescent labels, or cleavage sites. In some cases, a sequence-specific capture probe provided herein can include a spacer sequence. For example, a sequence-specific capture probe provided herein can contain biotin followed by a molecular spacer (e.g., 5, 6, 7, 8, 9, 10, 11, 12, 13, 14, 15, 16, 17, 18, 19, or 20 carbon atoms) followed by a nucleic acid sequences designed to hybridize with particular target nucleic acids. In some cases, a sequence-specific capture probe provided herein can contain a nucleic acid sequences designed to hybridize with particular target nucleic acids followed by a molecular spacer followed by biotin. The sequence-specific probe is not limited to a particular length. For example, in some embodiments, the probe length is between 35-55 nucleic acid bases (e.g., 30 bases, 35 bases, 40 bases, 42 bases, 50 bases, 54 bases, 55 bases, 60 bases).

After particular target nucleic acids present in a complex macromolecular mixture anneal to sequence-specific capture probes provided herein, the sequence-specific capture probes can be isolated together with the captured target nucleic acids. The present invention is not limited to a particular manner of isolating captured nucleic acids. Indeed, captured nucleic acids may be analyzed and resolved by a number of methods including solid phase and solution-based approaches including, but not limited to, electrophoresis (on a variety of supports including acrylamide or agarose gels, paper, etc.), chromatography, fluorescence polarization, mass spectrometry and chip hybridization.

For example, in some embodiments, magnetic material designed to interact with a component of sequence-specific capture probes can be incubated with the sequence-specific capture probes. In some embodiments, the magnetic material can be magnetic beads. In some embodiments, the magnetic beads are modified with carboxylic acid. In some embodiments, the magnetic beads can be treated with streptavidin, which interacts with biotin when biotin is present on a sequence-specific capture probe. In such cases, the sequence-specific capture probe/target nucleic acid complexes can be captured by the magnetic beads. Once captured by the magnetic beads, a magnetic force can be used to retrieve the beads together with the sequence-specific capture probe/target nucleic acid complexes from the complex macromolecular mixtures. These retrieved complexes can be treated to release the desired target nucleic acids. In some cases, streptavidin coated wells can be uses instead of beads. In some cases, probes can be directly conjugated to a solid support (e.g., without the use of streptavidin/biotin) using, for example, the methods and materials set forth in U.S. Pat. No. 6,133,436.

As used herein, the terms "solid support" or "support" refer to any material that provides a solid or semi-solid structure with which another material can be attached. Such materials include smooth supports (e.g., metal, glass, plastic, gold, diamond, silicon, and ceramic surfaces) as well as textured and porous materials. Such materials also include, but are not limited to, gels, rubbers, polymers, and other non-rigid materials. Solid supports need not be flat. Supports include any type of shape including spherical shapes (e.g., beads). Materials attached to solid support may be attached to any portion of the solid support (e.g., may be attached to an interior portion of a porous solid support material). Preferred embodiments of the present invention have biological molecules such as nucleic acid molecules and proteins attached to solid supports. A biological material is "attached" to a solid support when it is associated with the solid support through a non-random chemical or physical interaction. In some preferred embodiments, the attachment is through a covalent bond. However, attachments need not be covalent or permanent. In some embodiments, materials are attached to a solid support through a "spacer molecule" or "linker group." Such spacer molecules are molecules that have a first portion that attaches to the biological material and a second portion that attaches to the solid support. Thus, when attached to the solid support, the spacer molecule separates the solid support and the biological materials, but is attached to both.

Briefly, examples of insoluble supports include beads (silica gel, controlled pore glass, magnetic beads, biomagnetic separation beads such as Dynabeads®, Wang resin; Merrifield resin, which is chloromethylated copolystyrene-divinylbenzene (DVB) resin, Sephadex®/Sepharose® beads, cellulose beads, etc.), capillaries, flat supports such as glass fiber filters, glass surfaces, metal surfaces (steel, gold, silver, aluminum, silicon and copper), plastic materials including multiwell plates or membranes (e.g., of polyethylene, polypropylene, polyamide, polyvinylidenedifluoride), wafers, combs, pins or needles (e.g., arrays of pins suitable for combinatorial synthesis or analysis) or beads in an array of pits or nanoliter wells of flat surfaces such as wafers (e.g. silicon wafers), wafers with pits with or without filter bottoms.

An appropriate bead can included any three dimensional structure that can be conjugated to a solid support and provides an increased surface area for binding of DNA. Preferably, a bead is of a size in the range of about 1 to about 100 µm in diameter. In some cases, a bead can be made of virtually any insoluble or solid material. For example, a bead can be composed of silica gel, glass (e.g., controlled-pore glass (CPG)), nylon, Wang resin, Merrifield resin, Sephadex®, Sepharose®, cellulose, magnetic beads, Dynabeads®, a metal surface (e.g. steel, gold, silver, aluminum, silicon and copper), a plastic material (e.g., polyethylene, polypropylene, polyamide, polyester, polyvinylidenedifluoride (PVDF)) and the like. Beads can be swellable, e.g., polymeric beads such as Wang resin, or non-swellable (e.g., CPG).

As used herein, the term "conjugated" refers to ionic or covalent attachment. Preferred conjugation means include: streptavidin- or avidin-to biotin interaction; hydrophobic interaction; magnetic interaction (e.g., using functionalized Dynabeads); polar interactions, such as "wetting" associations between two polar surfaces or between oligo/polyethylene glycol; formation of a covalent bond, such as an amide bond, disulfide bond, thioether bond, or via crosslinking agents; and via an acid-labile linker. In some cases for conjugating nucleic acids to beads, the conjugating means can introduce a variable spacer between the beads and the nucleic acids. In some cases, the conjugation can be photocleavable (e.g., streptavidin- or avidin- to biotin interaction can be cleaved by a laser, for example for mass spectrometry). Appropriate cross-linking agents can include a variety of agents that are capable of reacting with a functional group present on a surface of the bead, insoluble support and or nucleic acid and with a functional group present in the nucleic acid and/or bead, respectively.

Reagents capable of such reactivity include homo- and hetero-bifunctional reagents, many of which are known in the art. A bifunctional cross-linking agent can be N-succinimidyl (4-iodoacetyl)aminobenzoate (SIAB). However, other crosslinking agents, including, without limitation, dimaleimide, dithio-bis-nitrobenzoic acid (DTNB), N-succinimidyl-S-acetyl-thioacetate (SATA), N-succinimidyl-3-(2-pyridyldithio)propionate (SPDP), succinimidyl 4-(N-maleimidomethyl)cyclohexane-1-carboxylate (SMCC) and 6-hydrazinonicotimide (HYNIC) can be used. In some cases, the cross-linking agent can be selected to provide a selectively cleavable bond when the nucleic acid molecule is immobilized on the insoluble support. For example, a photolabile cross-linker such as 3-amino-(2-nitrophenyl)propionic acid can be used to provide a means for cleaving the nucleic acid from the beads or insoluble (e.g., solid) support, if desired. For further examples of cross-linking reagents, see, e.g., Wong, "Chemistry of Protein Conjugation and Cross-Linking," CRC Press (1991), and Hermanson, "Bioconjugate Techniques," Academic Press (1995).

In some cases, a covalent amide bond can be formed between a bead and a insoluble support by reacting a carboxyl-functionalized bead with an amino-functionalized solid support (e.g., by reacting a carboxyl-functionalized Wang resin with an amino-functionalized silicon surface). In some cases, a carboxyl-functionalized support can be reacted with an amino-functionalized bead, which can take advantage of an acid-cleavable bifunctional trityl protection scheme employed for nucleic acid attachment. The bifunctional trityl linker can also be attached to the 4-nitrophenyl active ester on a resin (e.g. Wang resin) via an amino group as well as from a carboxy group via an amino resin.

In the bifunctional trityl approach, the beads may require treatment with a volatile acid (e.g., formic acid, trifluoracetic acid, etc.) to ensure that the nucleic acid is cleaved and can be removed. In which case, the nucleic acid can be deposited as a beadless patch at the bottom of a well in the solid support or on the flat surface of the solid support. After addition of matrix solution, the nucleic acid can then be desorbed into the mass spectrometer, for example.

The hydrophobic trityl linkers can also be exploited as acid-labile linkers by using a volatile acid or an appropriate matrix solution (e.g., a matrix solution containing, for example, 3-hydroxypicolinic acid (3-HPA) to cleave the aminolink trityl group from the nucleic acid molecule). In some cases, the acid lability can be changed. For example, trityl, monomethoxy, dimethoxy- or trimethoxytrityl can be changed to the appropriate p-substituted and even more acid labile tritylamine derivatives of the nucleic acids (i.e., trityl ether and tritylamine bonds to the nucleic acid can be made). Therefore, the nucleic acid can be removed from the hydrophobic linker, for example, by disrupting the hydrophobic attraction or by cleaving tritylether or tritylamine bonds under acidic or the usual mass spectrometry conditions (e.g., wherein the matrix, such as 3-HPA acts as an acid).

As pointed out above, the bead can also be associated with the solid support by non-covalent interactions. For example, a magnetic bead (e.g., a bead capable of being magnetized, e.g., a ferromagnetic bead) can be attracted to a magnetic solid support, and can be released from the support by removal of the magnetic field. In some cases, the bead can be provided with an ionic or hydrophobic moiety, which can associate with, respectively, an ionic or hydrophobic moiety of the solid support. Also, a bead can be provided with a member of a specific binding pair, and become immobilized to a solid support provided with a complementary binding moiety. For example, a bead coated with avidin or streptavidin can be bound to a surface coated with biotin or derivatives of biotin such as imino-biotin. It will be appreciated that the binding members can be reversed, e.g., a biotin-coated bead can bind to a streptavidin-coated solid support. Other specific binding pairs including hormone-receptor, enzyme-substrate, nucleic acid-complementary nucleic acid, antibody-antigen, and the like can be uses as described herein.

Examples of binding pairs or linker/interactions are listed in Table 1 of U.S. Pat. No. 6,133,436.

A sequence-specific capture probe can be designed to capture any particular target nucleic acid including, without limitation, cancer markers (e.g., kras codon 12 mutations, vimentin CpG hypermethylation, Bat26 MSI, and APC exon 15 insertion/deletions), infectious disease markers (e.g., rotavirus, enteric adenovirus, cryptosporidium, and H. pylori sequence fragments), and inflammatory disease markers (e.g., elevated human alu levels and pathogenic nucleic acid signatures). In some cases, a combination of different sequence-specific capture probes (e.g., three different sequence-specific capture probes designed to capture three different cancer markers) can be used.

A magnetic material can contain any appropriate material or combination of materials capable of being attracted to a magnetic field. For example, sequence-specific capture probe/target nucleic acid complexes can be retrieved using a paramagnetic (e.g., magnesium, molybdenum, lithium, and tantalum), ferromagnetic (e.g., iron, nickel, and cobalt), or superparamagnetic material (e.g., a particle or nanoparticle).

In some cases, the methods provided herein can include (a) using sequence-specific capture probes directly attached to magnetic materials to anneal with particular target sequences present in a complex macromolecular mixture and (b) magnetically capturing at least some of the magnetic materials having sequence-specific capture probes that annealed to the target nucleic acid. The magnetically captured magnetic materials can be treated so that the target nucleic acid can be released and collected. Any type of attachment can be used to attach sequence-specific capture probes and a material capable of being attracted to a magnetic field. For example, a sequence-specific capture probe and paramagnetic, ferromagnetic, or superparamagnetic material can be chelated.

In one embodiment, the methods and material provided herein can be used to collect a stable, particulate free, stool and buffer homogenate. For example, a stool sample can be collected using a stool collection device provided here. The stool collection device can contain a buffer provided herein such that nucleic acid and polypeptides present in the stool sample are stabilized. The ratio of buffer to stool (v/w) can vary from 2:1 to 10:1 (e.g., 3:1, 4:1, 7:1, 10:1). In some embodiments, the ratio of buffer to stool (v/w) is 7:1. The sample can be filtered or centrifuged to remove particulates. In some cases, the sample can be homogenized, centrifuged, and filtered. At this point, the nucleic acid (e.g., DNA) can be denatured (e.g., heat denatured), and sequence-specific capture probes and material capable of being attracted to a magnetic field can be added. For example, the sample can be heat denatured in the presence of excess biotinylated sequence-specific capture probes and hybridized overnight in a concentrated chaotrope solution (e.g., urea about 6-8 mol/L; guanidinium isothiocynate about 6 mol/L; or lithium trichloroacetate about 4.5 mol/L). Streptavidin coated magnetic beads can be used to effect separation of the hybridized fragments, which can then be eluted with a low salt buffer.

The invention will be further described in the following examples, which do not limit the scope of the invention described in the claims.

EXAMPLES

Example 1

Buffers for Stabilizing Nucleic Acids and Polypeptides in Stool

Three experiments were undertaken to assess the effect of stability buffer on stool DNA integrity. In the first experiment, four Stool samples were collected from clinically normal individuals and homogenized separately in both water and a buffer consisting of 0.5 M tris, 150 mM CDTA, and 10 mM NaCl. All samples were diluted to a final ratio of 1:7 (w/v) stool to water/buffer, centrifuged and filtered to remove insoluble materials. 1 µg of purified human DNA (Novagen) was spiked into 100 g stool equivalents from each homogenate. Aliquots were taken immediately (time 0) and at 3 and 5 days. (Incubation temperature –24° C.). DNA was precipitated with isopropanol, dissolved in TE buffer, and diluted 1:100 in nuclease-free water. Samples were amplified quantitatively with a SYBR green master mix on a Bio-Rad iCycler. Human DNA standards were used in the assay to assess fragment copy number. Two primers sets were specific for 160 and 60 bp fragments of the human gene apo(a).

Figure 5:
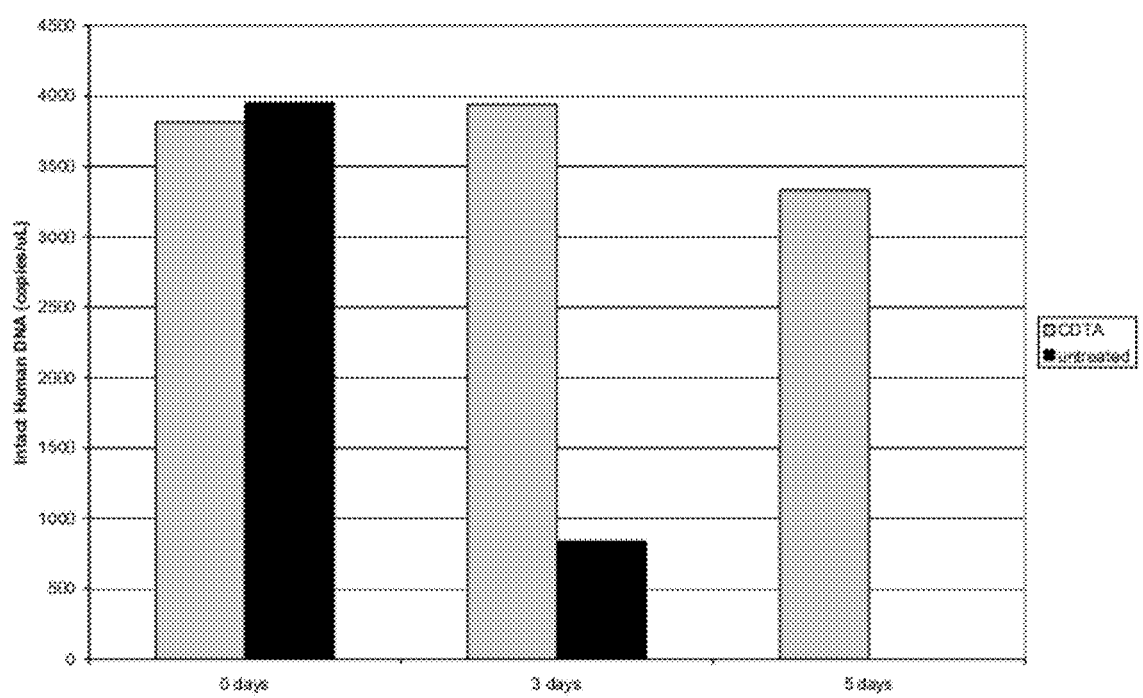
FIG. 5 is a histogram demonstrating the effect of ProDNA buffer on DNA stability in stool samples over time. 1 µg of human DNA was spiked into 100 mg of stool homogenate and incubated with or without 250 µL of ProDNA buffer at 24° C. for 5 days. Aliquots were taken at 0, 3, and 5 days from which DNA was extracted by isopropanol precipitation. Crude DNA preps were diluted 1:100 in water and quantitatively amplified with apo(a) human gene specific primers. Results were normalized to human DNA standards.

The results were as follows (Tables 1 and 2; FIG. 5).

TABLE 1

Long Amplicon (160 bp) 4 sample copy number averages

|  | Time 0 | 3 days | 5 days |
|---|---|---|---|
| stability buffer | 1915 | 1480 | 1968 |
| water | 1915 | 67 | <1 |

TABLE 2

Short Amplicon (60 bp) 4 sample copy number averages

|  | Time 0 | 3 days | 5 days |
|---|---|---|---|
| stability buffer | 3602 | 3942 | 3332 |
| water | 3602 | 839 | <1 |

The results demonstrate that the use of stability buffer allows for stable amplicon copy numbers at 3 and 5 days from initial sample prep. Thus, DNA degradation appears to be inhibited by the immediate addition of the buffer to the sample. The mechanism of action can be the sequestering or chelation of divalent cations by the CDTA reagent in the buffer. Since the operation of intestinal endonucleases and exonucleases requires divalent cations as cofactors, when such cofactors are limiting, the activity of the nucleases can decrease dramatically.

In the second experiment, the effect of temperature on stool DNA was assessed. Stools from two normal individuals were collected and processed as described above. The samples, in this case, were not spiked with extra human DNA. Two incubation temperatures were used; 24° C. and 49° C., the latter approximating the upper temperature limit of what samples might be subjected to in practice. Aliquots were taken at time zero, and at one and three days. DNA was precipitated and diluted as described above. Primers specific for human alu sequences were used in the qPCR reaction. Three different amplicon sizes were queried –45 bp, 130 bp, and 245 bp.

The results were as follows (Table 3).

TABLE 3

|  | W0 | W-22C-24 | W-22C-72 | W-49C-24 | W-49C-72 | B0 | B-22C-24 | B-22C-72 | B-49C-24 | B-49C-72 |
|---|---|---|---|---|---|---|---|---|---|---|
| | | | | | Stool #1 | | | | | |
| alu 245 | 0.27 | 0.2 | 0.21 | 0.25 | 0.2 | 181 | 182 | 229 | 2320 | 495 |
| alu 130 | 0.72 | 0.69 | 0.8 | 1.1 | 0.61 | 230 | 292 | 216 | 1770 | 421 |
| alu 45 | 1.76 | 1.35 | 2.76 | 1.18 | 0.49 | 342 | 364 | 261 | 1880 | 609 |
| | | | | | Stool #2 | | | | | |
| alu 245 | 0.19 | 0.27 | 0.25 | 0.24 | 0.19 | 1160 | 1150 | 1030 | 2120 | 570 |
| alu 130 | 0.83 | 0.8 | 0.83 | 0.69 | 4.39 | 1110 | 826 | 835 | 1590 | 480 |
| alu 45 | 1.16 | 1.13 | 0.85 | 1.25 | 1.16 | 1180 | 784 | 798 | 1110 | 513 |

In Table 3, W indicates water and B indicates buffer. The first and second numbers in the headings refer to temperature and # hours, respectively. FIG. 6 shows the data arranged in a bar graph format. The results demonstrate that the stability effect of the buffer is consistent at both incubation temperatures over a three day span.

The final experiment assessed the effects of the zwitterionic detergent in the stability buffer. It was first necessary to determine whether the inclusion of a zwitterionic detergent adversely affected the DNA stabilizing properties of the buffer. Stools from two normal individuals were collected and split into two 5 g fractions each. One fraction was treated with stability buffer minus the zwitterionic detergent, one with stability buffer plus 0.05% Zwittergent 3-16 detergent (CalbioChem, Cat. No. 693023, Lot No. B62555, MW 391.6), and the last with water. Dilutions were done at 1:7 (stool/buffer or water) ratios. Samples were homogenized and centrifuged. 500 µL of each supernatant was spiked with 1 µg of human DNA (Novagen). Aliquots were taken at time zero and at 3 days after a 24° C. incubation. Real time qPCR was performed as above. The primers utilized were human apo(a) "short" (60 bp) and alu "long" (245 bp). Alu PCR was performed on unspiked DNA.

The results were as follows (Table 4).

TABLE 4

|  | ALU 245 PCR Crude DNA 1:100 | | apo(a) "short" PCR Crude DNA 1:100 | |
|---|---|---|---|---|
|  | 0 hours | 72 hours | 0 hours | 72 hours |
| Sample 1 buffer | 628 | 715 | 751 | 1720 |
| Sample 2 buffer | 1240 | 1000 | 1660 | 3150 |
| Sample 1 buffer + zwittergent | 857 | 751 | 2940 | 3400 |
| Sample 2 buffer + zwittergent | 980 | 1030 | 5820 | 2970 |
| Sample 1 water |  | 2.01 |  | 618 |
| Sample 2 water |  | 7.51 |  | 268 |

The addition of the zwittergent did not significantly affect (beneficially or adversely) the ability of the buffer to preserve DNA integrity over time.

Secondly, some initial experiments were performed with a triple-quadrupole mass spectrometer to determine the effects of the zwittergent on protein and peptide stability in stool. Three human stool samples were collected and pooled. Five grams of pooled human stools were placed into each of four 50 mL Falcon tubes. Each tube received 12.5 mL of one of the following buffers: CDTA buffer, CDTA+Z pH8 buffer, CDTA+Z pH9 buffer, and ddH$_2$O (double deionized water). The CDTA buffer was produced to contain 150 mM CDTA (trans-1,2-Diaminocyclohexane-N,N,N',N'-tetraacetic acid monohydrate; Sigma, Cat. No.:125572-95-4; MW 364.35), 0.5 M Tris (Tris-HCL, Fisher Scientific, Cat. No.: BP152-1, Lot No. 045245, MW 121), and 10 mM NaCl (Curtis Matheson Scientific, Cat. No.: 832-006, Lot No.: M272 KPRB, MW 58) with the final pH of the buffer being 9.0. The CDTA+Z pH8 buffer was produced to contain the CDTA buffer plus 0.05% Zwittergent 3-16 detergent (CalbioChem, Cat. No.: 693023, Lot No.: B62555, MW 391.6) with the final pH of the buffer being 8.0. The CDTA+Z pH9 buffer was produced to contain the CDTA buffer plus 0.05% Zwittergent 3-16 detergent with the final pH of the buffer being 9.0. 40 µL of a 100 pmol/µL protein solution containing CEA (Carcinoembryonic Antigen; antigen grade, Human Metastatic Liver of colon Adenocarcinoma, Biodesign, Cat. No.: A3815, Lot No.: 5127106), Galectin-3 (human, recombinant, expressed in E. coli, Sigma, Cat. No.: G5170, Lot No.: 116K1383), and NNMT (Nicotinamide N-methyltransferase; recombinant, human, U.S. Biological, Cat. No.: N-2561-70, Lot No.: L7020957 C7020957, 50 µg) were added to each tube. The tubes were shaken with buffer until the stools were mostly homogenized. 2 mL of each sample was transferred to a 2-mL microcentrifuge tube and centrifuged for 10 minutes at 14,000 rpm. The supernatant was removed and pushed through a 0.2 µm syringe filter (Nalgene, Cat. No.: 190-2520, Lot No.: 595153). The filtrate was frozen, and the remaining stool homogenates were incubated at 24° C. After 72 hours, the remaining stool homogenates were shaken, centrifuged, and filtered as before.

The homogenates were desalted over StrataX columns and eluted in 2 mL of a solution containing 30% acetonitrile and 0.2% formic acid. The eluents were lyophilized, and quantitatively assessed by multiple reaction monitoring (MRM) using a triple—quadrupole mass spectrometric detection. This allows for a very accurate determination of intact peptide levels.

The results were as set forth in Table 5.

TABLE 5

| Key: (spike) 25 fmol CEA added (zwit) 0.001% zwittergent 3-16 | |
|---|---|
| 1) Water | 428585 |
| 2) Water spike | 814656 |
| 3) Water 72 hours | 738683 |
| 4) Water 72 spike | 4285859 |
| 1) CDTA | 356879 |
| 2) CDTA spike | 784406 |
| 3) CDTA 72 hours |  |
| 4) CDTA 72 spike | 814282 |
| pH 8.0 | |
| 1) CDTA zwit | no data |
| 2) CDTA zwit spike | 343523 |
| 3) CDTA zwit 72 hours | no data |
| 4) CDTA zwit 72 spike | 418282 |
| pH 9.0 | |
| 1) CDTA zwit | no data |
| 2) CDTA zwit spike | no data |
| 3) CDTA zwit 72 hours | no data |
| 4) CDTA zwit 72 spike | no data |

CEA was spiked into all test fractions to provide a baseline assessment for determining whether the zwittergent helps to stabilize the protein/peptide constituents of stool. The numbers in the above table represent peak areas of the CEA molecule. The data indicate that the zwittergent at the 0.001% concentration does not affect the stability of stool related peptides in either a positive or negative fashion. In fact, it appears that in terms of the variables of this study, water is as good as the buffer itself. However, the zwittergent by definition can allow for a more complete solubilization of peptides, thus affording a higher level of proteomic coverage with respect to the analysis of stool samples.

Tris/CDTA buffer and water are comparable in peak volume both before and after spiking. Addition of zwittergent 3-16 stabilizes spike experiment at pH 8.0, though there is minimal or absent signal for nascent stool in CDTA zwittergent/samples. Retention times for CEA peptide elution in higher pH samples were significantly lower than normal (3.5 minutes less, on average). This is likely due to poor column retention, perhaps caused by binding of basic analytes to active silanols. This could be an effect of the higher pH.

In conclusion, addition of zwittergent 3-16 can be done to help solubilize proteins and facilitate subsequent sample preparation. Addition of zwittergent 3-16 at 0.001% does not negatively affect stability of either proteins or nucleic acid markers within a stool matrix.

Example 2

Direct Capture of Specific Nucleic Acids from Complex Macromolecular Mixtures Five stool samples from clinically normal patients were collected in the presence of 250 mL stabilization buffer (formulation: 0.5 M tris, 150 mM EDTA, 10 mM NaCl; pH 9.0), and delivered to the processing lab the same day. The samples were homogenized, diluted with additional buffer to a final ratio of 1:7 (w/v) stool to buffer, centrifuged at 15,000×g, and filtered through a 0.45 micron filter to remove particulate. A 10 g stool equivalent aliquot was taken, and DNA was precipitated with isopropanol and sodium acetate. For each sample, 300 µL of stool supernatant and 300 µL of stool DNA were processed concurrently for capture of three distinct APC gene fragments.

Target gene sequences were enriched and purified from stool supernatant and stool DNA using sequence-specific capture. Each capture reaction was carried out by adding 300 µL of sample to an equal volume of 6 mol/L guanidine isothiocyanate solution (Sigma, St. Louis, Mo.) containing a pool of biotinylated sequence-specific oligonucleotides (10 pmol total). See, Table 6. The capture probes included a 5' C12 linker arm between the biotin and the first 5' base. After an overnight incubation at room temperature, 50 µL prepared Dynabeads® M-280 streptavidin (Invitrogen) was added to the solution, and it was incubated for one hour at room temperature. The bead/hybrid capture complexes were then washed 2 times with 1×B+W buffer (1.0 M NaCl, 5 mM Tris-HCl (pH 7.5), 0.5 mM EDTA), and the sequence-specific captured DNA was eluted into 40 µL 1×TE buffer by heat denaturation.

TABLE 6

Capture Probes.

| | | |
|---|---|---|
| APC MCR Probe 1 | CAGATAGCCCTGGACAAACCATGCCACCAAGCAGAAG | SEQ ID NO: 1 |
| MCR Probe 2 | TTCCAGCAGTGTCACAGCACCCTAGAACCAAATCCAG | SEQ ID NO: 2 |
| MCR Probe 3 | ATGACAATGGGAATGAAACAGAATCAGAGCAGCCTAAAG | SEQ ID NO: 3 |

Fragment copy numbers were determined by real time PCR using standards prepared from human DNA (Novagen). Samples were run in duplicate on a Bio-Rad iCycler using fragment specific primers:

```
APC C
5' TTCATTATCTTTGTCATCAGC 3'     SEQ ID NO: 4    250
                                                bp

5' CGCTCCTGAAGAAAATTCAA 3'      SEQ ID NO: 5

APC N
5' CAGGAGACCCCACTCATGTT 3'      SEQ ID NO: 6    346
                                                bp

5' TGGCAAAATGTAATAAAGTATC       SEQ ID NO: 7
AGC 3'

APC L2
5' GAGCCTCGATGAGCCATTTA 3'      SEQ ID NO: 8    192
                                                bp

5' TCAATATCATCATCATCTGAAT       SEQ ID NO: 9
CATC 3'
```

A correction factor of 8.67 was applied to the stool supernatant numbers to bring starting stool amounts into equivalence. The results are set forth in Table 7.

TABLE 7

DNA Extraction vs. Supernantant Capture Method.
DNA Extraction vs Supernantant Capture Method

| | DNA Extraction (copies/uL) | Supernatant (copies/uL) | Supernatant Adjusted (copies/uL) | Ratio SA:E |
|---|---|---|---|---|
| APC (C) Probe | | | | |
| sample 1480 | — | 8.82 | 77 | |
| sample 1481 | 33 | 13.1 | 115 | 3.5 |
| sample 1483 | 3000 | 352 | 3080 | 1.0 |
| sample 1484 | 92.5 | 8.93 | 78 | 0.8 |
| sample 1485 | 56.5 | 35.8 | 313 | 5.5 |
| APC (N) Probe | | | | |
| sample 1480 | — | 12.7 | 111 | |
| sample 1481 | 18.4 | 2.9 | 25 | 1.4 |
| sample 1483 | 2530 | 212 | 1855 | 0.7 |
| sample 1484 | 74.6 | 8.56 | 75 | 1.0 |
| sample 1485 | 31.5 | 21.8 | 191 | 6.1 |
| APC (L2) Probe | | | | |
| sample 1480 | — | 17.8 | 156 | |
| sample 1481 | 51.4 | 19.9 | 174 | 3.4 |
| sample 1483 | 4460 | 499 | 4366 | 1.0 |
| sample 1484 | 180 | 18.4 | 161 | 0.9 |
| sample 1485 | 135 | 84.8 | 742 | 5.5 |

The results are presented as the number of fragment copies captured from stool DNA and from unextracted stool supernatant. Column 1 lists the sample identifiers for the three APC fragment regions. Column 2 is the number of copies/µL from stool DNA as determined by qPCR. Column 3 is the number of copies/µL from unextracted stool supernatant. Column 4 normalizes the amount of starting material between both sets of data: Different amounts of samples were used for the direct (stool supernatant) vs. indirect (DNA) approach. The adjusted figures allow for a 1:1 comparison between the two methodologies. The final column is the ratio of column 4 figures over column 2 figures. The results indicate that direct capture is at least as good as capture from more highly purified starting material (DNA). In many cases, it is better. Since capture from DNA requires extra and more extensive processing, direct capture appears to be a less expensive, higher yielding procedure.

In another experiment, the capture method was used on three samples, two of which were also spiked with tp53 specific exon fragments. A probe complementary to this exon was used in the capture reaction. Methods were similar to methods described above.

The results are set forth in Table 8.

TABLE 8

| Ct = 250 | 1204 Spike | 1203 Spike | 1204 | 1203 | 1202 | water |
|---|---|---|---|---|---|---|
| DNA | 2,920,000 | 2,802,000 | 18,260 | 10,350 | 14,310 | 1.39 |
| Supernatant | 1,847,100 | 1,363,700 | 11,800 | 3,440 | 27,130 | |
| % recovery | 0.63 | 0.49 | 0.65 | 0.33 | 1.9 | |

DNA Extraction vs. Supernatant Capture Method

The results in this experiment complement the earlier study in that direct capture is shown to be a viable method of selecting and purifying specific sequences from highly heterogeneous biological solutions. The figures presented are tp53 fragment copies/µL (normalized). The spiked samples demonstrate the wide dynamic range for this procedure; it is not limited with respect to high copy numbers. Water is included here as a negative amplification control.

Example 3

The representativeness of DNA markers in stool samples using a convenient scoop-device of the present invention with whole stool homogenates was investigated. Whole stools from 20 patients with colorectal cancer were collected in bucket containers, sealed, and promptly sent to the process laboratory. In the laboratory, a 5 g sample was obtained with the scoop-device, 20 ml of stabilization buffer was added, vortexed, and stored at −80 C until assay. To the whole stool, 250 ml of buffer was added, the stool homogenized using a stomacher, and homogenates stored at −80 C in 30 ml ampules. When 20 stools had been obtained, human DNA concentrations were determined in blinded fashion by a previously described Alu method (see, e.g., Zou et al. Cancer Epidemiol Biomarkers Prev 2006, 15(6):1115-9; herein incorporated by reference in its entirety) on aliquots from scooped and whole stool homogenates. The results demonstrated a highly significant correlation (R2=0.93) between obtained Alu human DNA for samples collected via whole stool homogenate and via a stool sample collected with a scoop-device of the present invention.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for stabilizing nucleic acid and polypeptides within a stool sample, said method consisting of contacting said stool sample with a buffer, said buffer consisting of between about 100 to about 300 mM of a chelating agent, between about 400 and about 600 mM of tris hydrochloride, between about 5 and about 15 mM of NaCl, and between about 0 and about 0.075% of a zwitterionic reagent.

2. The method of claim 1, wherein said chelating agent is trans-1,2-Diaminocyclohexane-N,N,N',N'-tetraacetic acid monohydrate.

3. The method of claim 1, wherein said chelating agent is EDTA.

4. The method of claim 1, wherein said zwitterionic reagent is n-Hexadecyl-N,N-dimethyl-3-ammonio-1-propanesulfonate.

5. The method of claim 1, wherein said between about 100 to about 300 mM of a chelating agent is 150 mM trans-1,2-Diaminocyclohexane-N,N,N',N'-tetraacetic acid monohydrate.

6. The method of claim 1, wherein said between about 400 and about 600 mM of tris hydrochloride is 0.5 M tris hydrochloride.

7. The method of claim 1, wherein said between about 5 and about 15 mM of NaCl is 10 mM NaCl.

8. The method of claim 1, wherein said between about 0 and about 0.075% of a zwitterionic reagent is 0.05% n-Hexadecyl-N,N-dimethyl-3-ammonio-1-propanesulfonate.

9. The method of claim 1, wherein said buffer comprises 150 mM trans-1,2-Diaminocyclohexane-N,N,N',N'-tetraacetic acid monohydrate, 0.5 M tris hydrochloride, 10 mM NaCl, and 0.05% n-Hexadecyl-N,N-dimethyl-3-ammonio-1-propanesulfonate.

* * * * *